United States Patent
Ding et al.

(10) Patent No.: US 10,266,812 B2
(45) Date of Patent: Apr. 23, 2019

(54) LACCASE PRODUCING COMPOSITION

(71) Applicant: Jiangnan University, Wuxi (CN)

(72) Inventors: Zhongyang Ding, Wuxi (CN); Chaolin Guo, Wuxi (CN); Liting Zhao, Wuxi (CN); Bingxin Lu, Wuxi (CN); Qiong Wang, Wuxi (CN); Lin Peng, Wuxi (CN); Jian Lu, Wuxi (CN); Zhenghua Gu, Wuxi (CN); Guiyang Shi, Wuxi (CN)

(73) Assignee: Jiangnan University, Wuxi, Jiangsu (CN)

(*) Notice: Subject to any disclaimer, the term of this patent is extended or adjusted under 35 U.S.C. 154(b) by 0 days.

(21) Appl. No.: 15/268,892

(22) Filed: Sep. 19, 2016

(65) Prior Publication Data
US 2018/0002677 A1    Jan. 4, 2018

(51) Int. Cl.
*A61K 38/44* (2006.01)
*C12N 9/02* (2006.01)
*C12P 39/00* (2006.01)
*C12P 1/02* (2006.01)
*C12R 1/645* (2006.01)

(52) U.S. Cl.
CPC ............... *C12N 9/0061* (2013.01); *C12P 1/02* (2013.01); *C12P 39/00* (2013.01); *C12R 1/645* (2013.01); *C12Y 110/03002* (2013.01)

(58) Field of Classification Search
None
See application file for complete search history.

(56) References Cited

U.S. PATENT DOCUMENTS 8,907,165 B2 * 12/2014 Vacharathit ............ C12N 15/80
                                                        435/171

OTHER PUBLICATIONS

Spina et al. (Environmental Engin. & Mgmt J., vol. 14, No. 7, pp. 1743-1750, Jul. 2015).*
Alves et al. (Appl. & Environ. Microbiol., vol. 70, No. 11, Nov. 2004, pp. 6379-6384).*
Wang et al. (J.F.S., vol. 72, No. 8, 2007, pp. M325-M329).*
Piscitelli et al. (Bioengeered Bugs, vol. 1, iss. 4, p. 252-262).*
Thurston (Microbiol., vol. 140, pp. 19-26, 1994).*
Wang et al. (Process Biochem., vol. 50, 2015, pp. 901-905).*
Buzzini et al. (Canadian J. Microbiol., vol. 53, p. 1024-1031, 2007).*
Sun et al. (Int'l J. of Food Microbiol., vol. 94, pp. 263-267).*

* cited by examiner

*Primary Examiner* — Hope A Robinson
(74) *Attorney, Agent, or Firm* — IPro, PLLC; Na Xu

(57) ABSTRACT

The present invention provides a novel method for improving microbial laccase production, which relates to the field of microbial fermentation. The present invention is to add β-carotene and other types of carotenoids, or microorganisms that produce carotenoids, or mixtures comprising carotenoids into a fermentation system during fermentation of *Pleurotus ferulae* and other higher fungi. The present invention can improve the laccase production 12 times more than before, with the advantages of a simple process and high yield.

5 Claims, No Drawings

LACCASE PRODUCING COMPOSITION

CROSS-REFERENCES AND RELATED APPLICATIONS

This application claims the benefit of priority to Chinese Application No. 201610507284.2, entitled "A novel method for improving microbial laccase production", filed Jun. 30, 2016, which is herein incorporated by reference in its entirety.

BACKGROUND OF THE INVENTION

Field of the Invention

The present invention relates to the field of microbial fermentation, which relates to a novel method for improving microbial laccase production.

Description of the Related Art

Laccase (p-diphenoloxidase, EC 1.10.3.2) are a group of blue multicopper oxidases that are capable of oxidizing mono-, di- and polyphenols, aminophenols, methoxyphenols, aromatic amines and ascorbic acid. Various substrates can be oxidized by laccase catalysis, which extends the industrial application in pulp and paper industry, wastewater treatment industry, organic synthesis and so on.

Laccase is mostly produced from filamentous fungi, especially basidiomycetes and ascomycetes fungi. However, low laccase production from ascomycetes and basidiomycetes could hardly meet the growing demand for industrial utilization of laccase. Besides the bacteria, nutrients, and cultivation conditions, some kinds of stimulators affects the laccase production by basidiomycetes and ascomycetes. The copper ions is one of the compositions of laccase activity center and an effective stimulator for laccase synthesis as well. Meanwhile, some small-molecules aromatic compounds including guaiacol, veratryl alcohol, vanillin and cinnamic acid are also used as stimulators for improving laccase production because of the structure similarity to the lignin. However, the simulators are found to be usually very expensive, which lead to higher cost in laccase production. Meanwhile, production with addition of copper ions or aromatic compounds induces pollution to the environment, and results to following detoxification treatment for culture, which influences the industrialization of laccase application. A novel, economic, safe and efficient stimulator is necessary and will surely be an important researching direction for improving laccase production. It may also inject new energies into microbial fermentation and industrial production.

DETAILED DESCRIPTION

The first goal of the present invention is to provide a novel stimulator for microbial laccase production by a laccase-producing microorganism.

An active ingredient of the stimulator comprises carotenoid, and the stimulator comprises one or more types of the carotenoids.

The laccase-producing microorganism comprises a laccase-producing filamentous fungi.

In one embodiment, the stimulator is β-carotene, lycopene, or both.

In one embodiment, the filamentous fungi comprises *Pleurotus ferulae, Trametes versicolor, Pleurotus ostreatus*, or *Ganoderma lucidum*.

In one embodiment, the active ingredient of the stimulator comprises carotenoids, or one or more carotenoids-producing microorganisms, or extracts of carotenoids.

Another goal of the present invention is to provide a novel method for improving microbial laccase production, and the method comprises adding the stimulator during a fermentation process.

In one embodiment, the laccase-producing microorganism comprises a filamentous fungi which is able to produce laccase.

In one embodiment, the laccase-producing microorganism comprises *Pleurotus ferulae, Trametes versicolor, Pleurotus ostreatus*, or *Ganoderma Lucidum*.

In one embodiment, the stimulators comprises compounds of carotenoids, or a mixture comprising carotenoids; and the method comprises choosing or adjusting amount of the stimulator and time of adding the stimulator according to a condition of the fermentation process; wherein the mixture comprising carotenoids comprises an active laccase-producing microorganism, an inactivated laccase-producing microorganism, or extracts of carotenoids; and the active laccase-producing microorganism comprises *Rhodotorula mucilaginosa, Phaffia rhodozyma, Sporidiobolus pararoseus*, or *Rhodotorula glutinis*.

In one embodiment, the microorganism is bacteria or fungi that frequently used in this field; the cultivation method is common methods used in this field.

In one embodiment, the amount of carotenoids is 0.1~30 mg/L, the carotene is dissolved in acetone, sterilized through hydrophobic membrane to remove bacteria, and then evaporated to dryness through rotary evaporator; the obtained substrates are then dissolved in sterilized oil and added into fermentation medium.

The mixture comprising carotenoids comprises an active laccase-producing microorganism or an inactivated laccase-producing microorganism, or extract comprising carotenoids.

In one embodiment, the method comprises cultivating an active carotenoids-producing microorganism, and adding an appropriate amount of the carotenoids-producing microorganism into the fermentation process for co-culture for a pre-determined amount of time.

In one embodiment, before being added into the fermentation system, inactivated carotenoids-producing organism is obtained through water bath under 70° C. for 1 h.

In one embodiment, the extract comprising carotenoids is obtained according to the following steps: (1) cells are disrupted by alternate freezing and thawing, and then heated under 70° C. for 1 h, (2) after centrifugation, removing the supernatant and adding a certain volume of vegetable oil to the precipitate; extract through slight oscillation for 1 h and then oil extract is obtained and then been added into the fermentation system; the above operation is under a sterilized environment.

The advantage of the present invention includes:

1. Multiple addition modes for stimulators. The addition mode in the present invention includes: straightly adding carotenoids, adding extract of carotenoids, adding microorganism that producing carotenoids, and adding treated microorganism that producing carotenoids.

2. Wide application. The stimulators in the present invention have the ability of promoting a variety of microorganisms for laccase production.

3. Great promoting effect. The present invention provides a method for promoting laccase production through adding carotenoids or yeast cells that producing carotenoids, which increases laccase activity over twofold than that produced by *Pleurotus ferulae*; and 12 times than that produced by other higher fungi.

EXAMPLES

Enzyme Assay:

The standard assay comprised following steps: A 1 mL reaction mixture comprising 880 µL 0.1 mol·L$^{-1}$ acetic acid-sodium acetate (pH 4.5), 100 µL ABTS stock (final assay concentration 1 mol·L$^{-1}$) and 20 µL diluted enzyme (absorbance between 0.2~0.8) is incubated at 30° C. for 5 min, final absorbance is spectrophotometrically monitored at 420 nm.

One unit of enzyme was defined as the amount of enzyme that oxidied of 1 µmol ABTS per minute.

The enzyme activity is calculated according to the formula below:

$$\text{Enzyme activity}(U) = \frac{(A_2 - A_1) \times 50 \times 10^6}{t \times \varepsilon}$$

$A_1$—Absorbance of the blank;
$A_2$—Final absorbance;
t—Reaction time;
ε—molar absorptivity of ABTS, 3.6×10$^4$ L·mol$^{-1}$·cm$^{-1}$.

Determination of β-Carotene (1) Standard solution preparation: A 2 mg standard β-carotene or lycopene was accurately weighted and dissolved in chloroform in a 10 mL brown constant bottle, stored in the dark at −20° C.

(2) Sample preparation:

a) Determination of β-carotene or lycopene in culture broth: 80 mL culture broth and 80 mL chloroform were mixed and shaking-extracted for 15 min, the resulting chloroform was concentrated to 10 mL in rotary vacuum evaporator to prepare chloroform extract comprising β-carotene or lycopene;

b) Determination of β-carotene in *Rhodotorula mucilaginosa*: *Rhodotorula mucilaginosa* cell was disrupted by freeze-drying, 1 g cells was weighted and transferred to 5 mL EP tube, 2 mL chloroform is added and shaking-extracted for 15 min, the resulting chloroform was centrifuged, supernatant from which was volumed to 10 mL by adding chloroform to prepare chloroform extract comprising β-carotene.

c) Determination of β-carotene in co-culture broth: 150 mL culture broth was centrifuged, cells collected from that was fully grinded, shaking-extracted for 15 min with 80 mL chloroform addition, the resulting chloroform solution was concentrated to 10 mL in rotary vacuum evaporator to prepare chloroform extract comprising β-carotene.

(3) LC-MS detection:

LC condition: the UPLC system equipped with an Waters Acquity PDA detection and couples to WATERS MALDI SYNAPT Q-TOF MS was used for detection. The extracted β-carotene is separated using Waters Acquity UPLC BEH C18 column (2.1 mm×100 mm) with a column temperature of 45° C., a flow rate of 0.3 mL·mL$^{-1}$, an injection volume of 1 µL. The separation of β-carotene was achieved using a mobile phase consisting of acetonitrile/iso-propyl alcohol, 10:90, v/v (solvent A) and acetonitrile (solvent B). The mass spectrometer was optimized in ESI+ mode for the determination of β-carotene under following condition: capillary voltage: 3.5 kV, sample cone: 30 V; vaporizer temperature 330° C.; trap gas flow: 700 L·Hr$^{-1}$; collision energy: 6 eV; quality range: 100-1500; voltage detection 1800 V (4) The content of β-carotene was calculated according to the formula below:

$$m = \frac{m_1 \times A_2 \times V_2 \times 10}{m_2 \times A_1 \times V_1}$$

m: Content of β-carotene or lycopene in 10 mL sample (mg);
$m_1$: Content of β-carotene or lycopene in standard sample (mg);
$m_2$: Weight of sample (mg);
$A_1$: Peak area of standard sample;
$A_2$: Peak area of sample;
$V_1$: Weight of sample (µL);
$V_2$: Volume of sample (mL);

Example 1 Laccase Production Added with β-Carotene and Lycopene

Liquid medium (g·L$^{-1}$): glucose 20, corn meal 10, wheat bran 10, K$_2$SO$_4$ 0. 1742, pH 9.0; medium was used for seed culture and liquid fermentation for *P. ferulae*.

Seed preparation: 2 pieces of *P. ferulae* with an area of 0.5 cm$^2$ were transferred to 80 mL seed medium, incubated at 25° C. under 150 r·min$^{-1}$ for 7 d.

Laccase fermentation: 3% (v/v) seed culture broth was inoculated into 150 mL liquid medium, and then incubated at 25° C. under 150 r·min$^{-1}$ for 7 d.

4 mg β-carotene and 4 mg lycopene was respectively weighted and dissolved in acetone, 0.22 µm hydrophobic membrane was used to remove bacterial from the acetone solution. The sterile solution was transferred to 50 mL tube and then evaporated to dryness through rotary vacuum evaporator. The resulting dryness was collected and dissolved in 1.0 sterile vegetable oil. The wherein said oil was added into 2-day *P. ferulae* fermentation system and then continued fomenting for another 5 d. The fermentation without addition of β-carotene or lycopene was set as control. Content of β-carotene and lycopene were detected during the fermentation. Laccase was determined when the fermentation finished. It was shown that β-carotene concentration was 25.37 mg/L, 13.13 mg/L, 6.90 mg/L, 1.66 mg/L, and 0 mg/L respectively from the initial day to the 4$^{th}$ day of the fermentation, the lycopene in culture broth from those days was 24.83 mg/L, 3.22 mg/L, 1.59 mg/L, 0.31 mg/L and 0 mg/L, respectively.

Example 2 Laccase Production Added with *Rhodotorula mucilaginosa*

YPD medium (g·L$^{-1}$): peptone 20, yeast extract 10, glucose 20, at nature pH.

Seed preparation: colony of *R. mucilaginosa* was picked and inoculated into 80 mL YPD medium, incubated at 30° C. under 200 r·min$^{-1}$ for 48 h.

*P. ferulae* was incubated according to Example 1.

Co-culture of *P. ferulae* and *R. mucilaginosa*: 3% (v/v) *R. mucilaginosa* was inoculated when *P. ferulae* had been incubated for 48 h, both of the strains were then co-cultured for another 5 d. The *P. ferulae* fermentation without *R. mucilaginosa* addition was set as control. Laccase activity was determined when fermentation finished. Concentration of β-carotene was determined during fermentation process.

The results shows that content of β-carotene in culture broth was 0.0015 mg/L, 0.0040 mg/L, and 0.013 mg/L respectively on the $1^{st}$, $3^{rd}$, and $5^{th}$ day of co-culture.

The laccase activity from fermentation with *R. mucilaginosa* addition was 7630 $U \cdot L^{-1}$, while laccase activity in control group was only 3500 $U \cdot L^{-1}$.

Example 3 Laccase Production Added with *Phaffia rhodozyma, Sporidiobolus pararoseus* and *Rhodotorula glutinis*

*P. ferulae* was incubated according to Example 1.

*P. rhodozyma, S. pararoseus* and *R. glutinis* were incubated according to Example 2

*P. ferulae* was coincubated with *P. rhodozyma, S. pararoseus* and *R. glutinis* were incubated according to Example 2.

Experimental group: inoculation amount of *R. mucilaginosa* is 1.25 mL, 2.5 mL, 5 mL, and 10 mL respectively. Fermentation without *R. mucilaginosa* addition was set as control.

Laccase production of *Pleurotus ferulae* improved when inoculatet with *S. pararoseus* at an amount of 2.5 mL, 5 mL, and 10 mL. Besides, the laccase activity reached to peak at 10000 $U \cdot L^{-1}$ under 2.5 mL inoculation amount of *S. pararoseus*. The content of β-carotene was 0.027 mg/L, 0.036 mg/L, and 0.040 mg/L in culture broth respectively from the $1^{st}$, $3^{rd}$, and $5^{th}$ day of co-culture.

The laccase activity achieved to 7161 $U \cdot L^{-1}$ under 1.25 mL inoculation amount of *R. glutinis* when *P. ferulae* co-cultured with *R. glutinis*, while laccase activity was 3700 $U \cdot L^{-1}$ in control group.

Example 4 Laccase Production Added with Heat-Treated *Rhodotorula mucilaginosa*

*P. ferulae* was cultivated according to Example 1.

*R. mucilaginosa* was cultivated according to Example 2, and then respectively treated under 55° C., 60° C., 65° C., and 70° C. water-bath for 1 h.

High-temperature sterilized group (HTS group): *R. mucilaginosa* treated under 121° C. for 20 min.

Control group 1: fermentation without *R. mucilaginosa* addition.

Control group 2: fermentation with untreated *R. mucilaginosa*.

Spread plate was employed to evaluate the effect of different condition of heat treatment. It was shown that, colony number of *R. mucilaginosa* decreased for over 50% after heat-treated at 55° C. for 1 h. Higher temperature led to lower number of colonies. The effect of treatment under 70° C. or above for 1 h was the same with the effect of HTS group, both of which had a completely sterilization.

Cells of *R. mucilaginosa* from above groups with wet weight of 1.5 g, 3.0 g, 4.5 g, 6 g were added into *P. ferulae* fermentation system after 48-h incubation, continued fermenting for another 5 d, laccase activity were determined. The resulting culture broth involved with inactive *R. mucilaginosa* (treated under 70° C.) showed a high laccase activity. Besides, the laccase activity increased with the addition of cells. Laccase activity in broth with 6 g *R. mucilaginosa* addition achieved 7260 $U \cdot L^{-1}$.

Example 5 Laccase Production Added with Extract Comprising β-Carotene

*P. ferulae* was incubated according to Example 1.

*R. mucilaginosa* was incubated according to Example 2.

Cells of *R. mucilaginosa* was collected under aseptic condition. Wet weight of 4 g cells mixed with sterilize water was disrupted through repeated frozen and thawed, and then 70° C. treated for 1 h, centrifugation was employed to collect the precipitate from the solution. Sterilize vegetable oil with precipitate was mixed, extracted combined with shaking for 1 h to obtain the oil extract of *R. mucilaginosa*. The extract was added into 2-day fermentation system of *P. ferulae*. The fermentation was then continued for another 5 days and laccase in the culture broth was determined. Fermentation added with equivalent vegetable oil was set as control.

It was shown that, laccase production improved 35% after adding with 3 mL extract oil, which achieved a laccase activity of 4850 $U \cdot L^{-1}$.

Example 6 Laccase Production Added with *Rhodotorula mucilaginosa*

Higher fungi, such as *T. versicolor, P. ostreatus*, and *G. Lucidum* was coincubated with *R. mucilaginosa*.

*R. mucilaginosa* was cultivated according to Example 2.

Medium for *T. versicolor, P. ostreatus*, and *G. Lucidum* was: wheat bran 1%, corn meal 1%, glucose 2%, $MgSO_4 \cdot 7H_2O$ 0.2%, and $KH_2PO_4$ 0.3%.

Cultivation condition for *T. versicolor, P. ostreatus*, and *G. Lucidum*: inoculation volume 3%; incubation lasted 5 d, 6 d, and 8 d for *T. versicolor, P. ostreatus*, and *G. Lucidum*, respectively. *R. mucilaginosa* was inoculated at a volume of 0, 1.5%, 3%, 6% and laccase activities were determined after 5-day co-culture.

As the results, laccase activity was increased in fungi fermentation involved with *R. mucilaginosa*. The laccase produced by *T. versicolor* was 1873 $U \cdot L^{-1}$, it achieved 3797 $U \cdot L^{-1}$ with 6% *R. mucilaginosa* participated in fermentation. The laccase produced by *P. ostreatus* was 1147 $U \cdot L^{-1}$ with 3% *R. mucilaginosa* participated in fermentation, which was six fold of that in fermentation without *R. mucilaginosa* addition. The laccase produced by *G. Lucidum* was only 80.3 $U \cdot L^{-1}$, with increasing of *R. mucilaginosa* addition, it achieved 982.8 $U \cdot L^{-1}$, which improved 12 times than initial production.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A composition comprising a laccase-producing microorganism and a carotenoid; wherein the laccase-producing microorganism is *Sporidiobolus pararoseus*.

2. The composition of claim 1, wherein the carotenoid is β-carotene, lycopene or a mixture thereof.

3. A method of improving laccase production, comprising adding the composition of claim 1 during a fermentation process.

4. The method of claim 3, wherein the method comprises choosing or adjusting amount of the composition and time of adding the composition according to the fermentation process.

5. The method of claim 3, further comprising cultivating a carotenoid-producing microorganism, and adding an appropriate amount of the carotenoid-producing microorganism into the fermentation process for co-culture for a pre-determined amount of time.

* * * * *